United States Patent
Koshida et al.

(10) Patent No.: US 9,433,565 B2
(45) Date of Patent: Sep. 6, 2016

(54) HYDROPHILIC AND HIGHLY OIL ABSORBENT BORON NITRIDE POWDER, METHOD FOR MANUFACTURING THE SAME, AND COSMETIC

(71) Applicant: MIZUSHIMA FERROALLOY CO., LTD., Kurashiki-shi, Okayama (JP)

(72) Inventors: Takahisa Koshida, Kurashiki (JP); Masato Kumagai, Kurashiki (JP); Shoichi Hiwasa, Kurashiki (JP)

(73) Assignee: MIZUSHIMA FERROALLOY CO., LTD., Kurashiki-shi, Okayama (JP)

( * ) Notice: Subject to any disclaimer, the term of this patent is extended or adjusted under 35 U.S.C. 154(b) by 0 days.

(21) Appl. No.: 14/429,451

(22) PCT Filed: Aug. 27, 2013

(86) PCT No.: PCT/JP2013/005045
§ 371 (c)(1),
(2) Date: Mar. 19, 2015

(87) PCT Pub. No.: WO2014/049955
PCT Pub. Date: Apr. 3, 2014

(65) Prior Publication Data
US 2015/0209248 A1 Jul. 30, 2015

(30) Foreign Application Priority Data

Sep. 28, 2012 (JP) ................. 2012-218421

(51) Int. Cl.
*A61K 8/19* (2006.01)
*A61Q 1/02* (2006.01)
*C01B 21/064* (2006.01)
*A61K 8/02* (2006.01)

(52) U.S. Cl.
CPC ............... *A61K 8/19* (2013.01); *A61K 8/022* (2013.01); *A61K 8/0245* (2013.01); *A61Q 1/02* (2013.01); *C01B 21/064* (2013.01); *C01B 21/0648* (2013.01); *A61K 2800/412* (2013.01); *A61K 2800/651* (2013.01); *C01P 2004/20* (2013.01); *C01P 2004/50* (2013.01); *C01P 2004/61* (2013.01); *C01P 2006/12* (2013.01); *C01P 2006/19* (2013.01); *C01P 2006/80* (2013.01); *C01P 2006/90* (2013.01); *Y10T 428/2982* (2015.01)

(58) Field of Classification Search
None
See application file for complete search history.

(56) References Cited

FOREIGN PATENT DOCUMENTS

| JP | S5860603 A | | 4/1983 |
|----|-----------|---|--------|
| JP | S58181708 A | | 10/1983 |
| JP | 62100404 A | * | 5/1987 |
| JP | H01160811 A | | 6/1989 |
| JP | H04164805 A | | 6/1992 |
| JP | H05186205 A | | 7/1993 |
| JP | H07041311 A | | 2/1995 |
| JP | 2000302644 A | | 10/2000 |
| JP | 2012176910 A | * | 9/2012 |

OTHER PUBLICATIONS

Koshida Espacenet English translation of JP 2012176910A.*
Nov. 13, 2013 International Search Report issued in International Patent Application No. PCT/JP2013/005045.
Feb. 15, 2016, Office Action issued by the State Intellectual Property Office in the corresponding Chinese Patent Application No. 201380051157.0 with English language Search Report.
Mar. 15, 2016, Office Action issued by the Japan Patent Office in the corresponding Japanese Patent Application No. 2014-538116 with English language.

* cited by examiner

*Primary Examiner* — Robert A Wax
*Assistant Examiner* — Quanglong Truong
(74) *Attorney, Agent, or Firm* — Kenja IP Law PC

(57) ABSTRACT

A boron nitride powder including flat-shaped primary particles of BN and an aggregate of the primary particles has a water permeation speed not less than 1 mm$^2$/s and oil absorption of 100 ml/100 g to 500 ml/100 g, which is a cosmetic boron nitride powder with high hydrophilicity and high oil absorbency. The use of such a boron nitride powder provides a cosmetic that is significantly improved not only in gloss finish and transparency (bare skin feeling) but also in sustainability.

8 Claims, 1 Drawing Sheet

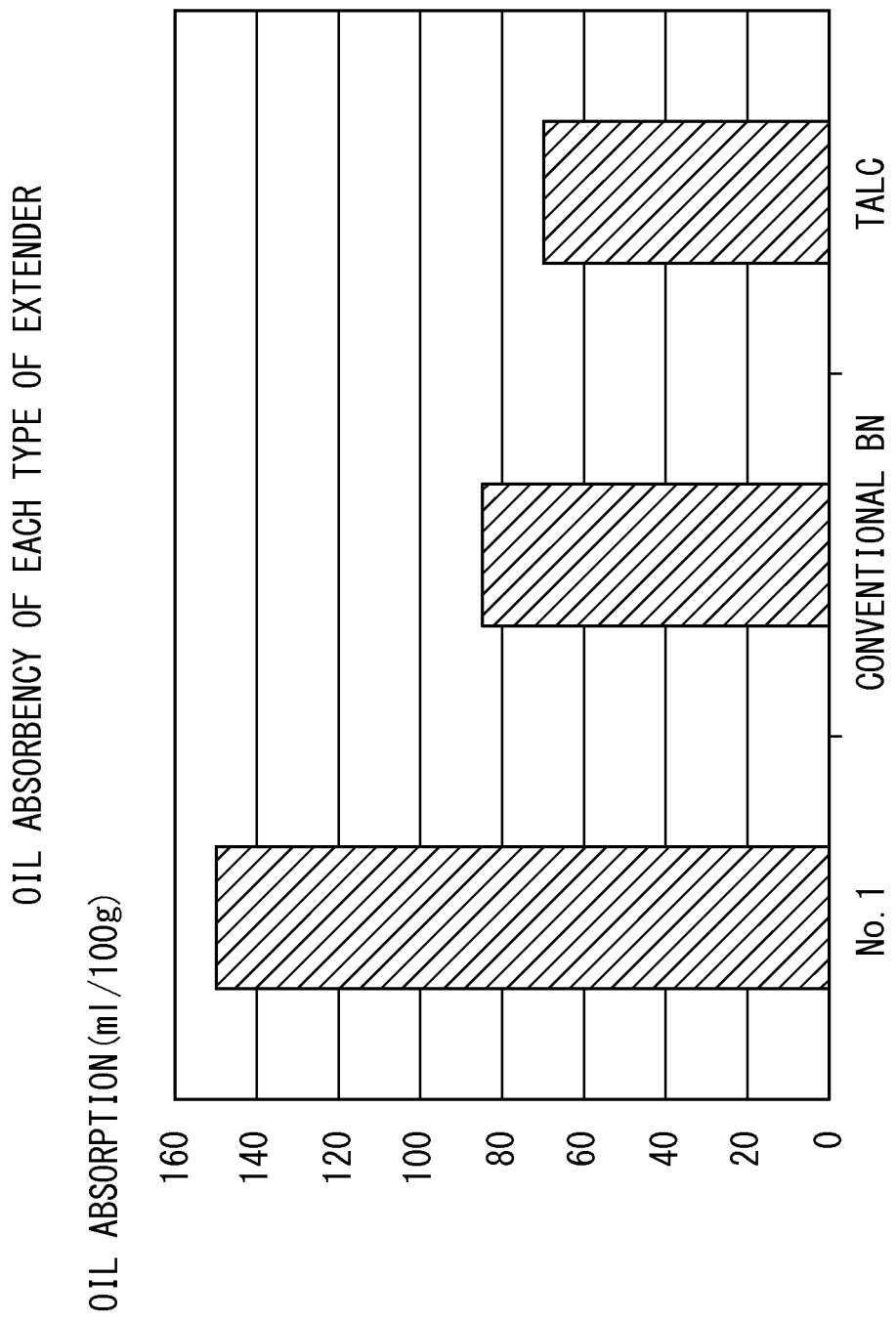

HYDROPHILIC AND HIGHLY OIL ABSORBENT BORON NITRIDE POWDER, METHOD FOR MANUFACTURING THE SAME, AND COSMETIC

TECHNICAL FIELD

This disclosure relates to a hydrophilic and highly oil absorbent boron nitride powder and a method for manufacturing the same, and is intended to advantageously improve the makeup sustainability in its application to a cosmetic.

The disclosure also relates to a cosmetic using the boron nitride powder.

The hydrophilic and highly oil absorbent boron nitride powder is particularly suitable for use in a water-based cosmetic such as liquid foundation among cosmetics. Such a water-based cosmetic has a high affinity for water and can be removed easily, and so is excellent for easy makeup.

BACKGROUND

A boron nitride powder (also referred to as a BN powder) has excellent lubricity as compared with other materials, and is gaining attention as a pigment for cosmetics (also referred to as cosmetic products). In particular, for its excellent lubricity, the BN powder is increasingly used as a cosmetic extender recently.

A cosmetic extender is a base for dispersing a color pigment, and significantly influences feelings of use such as "spreadability" (the property of being smoothly applied to the skin surface) and "sustainability" (the property of sustaining the state of application to the skin).

Conventional cosmetic extenders are mostly natural ores and resins, which are not always satisfactory in terms of usability, stability, etc. For example, inorganic materials such as talc, mica, and sericite have catalytic activities, which can degrade perfumes or oils and cause smell change. Resin materials such as nylon powder and polyethylene powder are chemically stable, but have a problem of poor formability.

The BN powder is excellent in spreadability and sustainability, as compared with natural ores and resins.

This is because the BN powder not only has excellent lubricity, but also is flat-shaped and so has appropriate coverage and adhesion.

JP H5-186205 A (Patent Literature (PTL) 1) and JP H7-41311 A (PTL 2) propose manufacturing methods for such BN powders. These manufacturing methods are expected to supply chemically stable, flat-shaped BN powders.

CITATION LIST

Patent Literatures

PTL 1: JP H5-186205 A
PTL 2: JP H7-41311 A

As mentioned above, a BN powder is increasingly used instead of conventional materials as it exhibits excellent effects of improving the properties of basic cosmetics.

Meanwhile, cosmetic users' desire to further enhance the evenness of application to the skin to make the skin look more beautiful is growing more and more. This spurs the development of various high-function new materials.

A BN powder used as the extender is required to have excellent compatibility with various constituent materials of the cosmetic, and also have excellent durability of effect, i.e. sustainability.

While liquid foundation is increasingly used for its ease of use particularly in recent years, a BN powder used for liquid foundation needs to have a hydrophilic surface because the BN powder, if not hydrophilic, does not evenly disperse in water.

To meet this demand, it could be helpful to provide a boron nitride powder for cosmetics that is hydrophilic and achieves significantly improved sustainability as compared with conventional techniques, together with an advantageous method for manufacturing the same.

It could also be helpful to provide a cosmetic that has significantly improved sustainability by use of the above-mentioned boron nitride powder, as compared with conventional techniques.

SUMMARY

As a result of conducting intensive study to fulfill the objects stated above, we have discovered that the sustainability of liquid foundation is closely related to the oil absorption of a BN powder contained. We have thus found that higher oil absorption of the BN powder contributes to better sustainability.

Since a BN powder is usually synthesized at high temperature, the end product is water repellent with no hydrophilic functional group being present on its surface. To make the BN powder hydrophilic, hydrophilic functional groups need to be provided on the surface after the synthesis.

Particularly in an existing process, firing at a high temperature not less than 1600° C. is performed to remove boric acid which is an impurity, and as a result almost no functional group remains on the surface of the BN powder.

In view of this, we have conducted various study on a method of providing functional groups on the surface of the BN powder.

A possible method of providing functional groups on the surface of the BN powder is to heat the BN powder at high temperature in the atmosphere so that functional groups are provided by BN oxidation. Actually, as a result of heating a BN powder in an oxidizing atmosphere of 300° C. or higher, the powder surface was able to be provided with functional groups to attain hydrophilicity. However, we have learned that, while the BN powder provided with surface functional groups by such oxidation treatment is hydrophilic, the functional groups are present in the form of —BOH and B dissolves in water, which damages the skin in the case where the BN powder is used in a cosmetic.

It is therefore necessary to suppress the leaching of B.

We have then studied a method of providing functional groups on the surface of the BN powder while suppressing the leaching of B.

As a result, we have found that the objects stated above can be fulfilled by performing washing treatment using a washing liquid that contains a polyoxyethylene surfactant.

We have also found that, since impurities are removed by the washing treatment, the BN powder obtained as a result of the washing treatment has significantly improved oil absorption as the dispersion of the aggregate powder is facilitated and the powder has more cavities, and thus exhibits significantly improved sustainability.

This disclosure is based on these findings.

In detail, we provide:

1. A hydrophilic and highly oil absorbent boron nitride powder including flat-shaped primary particles of BN and an aggregate of the primary particles, wherein a water permeation speed is not less than 1 mm$^2$/s, and oil absorption is 100 ml/100 g to 500 ml/100 g.

2. The hydrophilic and highly oil absorbent boron nitride powder according to the foregoing 1, wherein the primary particles of BN are flat-shaped with an average major diameter of 2 µm to 20 µm and a thickness of 0.05 µm to 0.5 µm.

3. The hydrophilic and highly oil absorbent boron nitride powder according to the foregoing 1 or 2, wherein an amount of soluble boron is less than or equal to 100 ppm.

4. The hydrophilic and highly oil absorbent boron nitride powder according to any of the foregoing 1 to 3, wherein a specific surface area is 1 $m^2/g$ to 10 $m^2/g$, and an oxygen content is less than or equal to 1.5 mass %.

5. A method for manufacturing a hydrophilic and highly oil absorbent boron nitride powder, the method including: heating at least one of boric acid and a dehydration product thereof, at least one of urea and a compound thereof, and boron carbide in an inert atmosphere to obtain a boron nitride powder having a turbostratic structure; heat-treating the obtained boron nitride powder at a temperature of 1500° C. to 2300° C. in an inert atmosphere; grinding the heat-treated boron nitride powder; and washing primary particles of boron nitride obtained as a result of the grinding in a washing liquid that contains a surfactant, and drying the washed primary particles.

6. A cosmetic including the boron nitride powder according to any of the foregoing 1 to 4.

7. The cosmetic according to the foregoing 6, wherein an amount of the boron nitride powder contained in the cosmetic is 0.1 mass % to 70 mass %.

8. The cosmetic according to the foregoing 6 or 7, wherein the cosmetic is liquid foundation.

Our boron nitride powders have excellent lubricity, and have the property of spreading like sliding with a light force. Hence, smooth extension can be achieved in inunction operation when using the cosmetic.

Moreover, our cosmetics have significantly improved sustainability as well as gloss finish and transparency because, when the boron nitride powder with improved hydrophilicity and oil absorbency is used in a water-based cosmetic such a liquid foundation, not only the excellent compatibility of the boron nitride powder eases uniform mixing but also the resistance to sweat and the like secreted from the skin is increased.

BRIEF DESCRIPTION OF THE DRAWINGS

FIG. 1 is a diagram illustrating the oil absorbency of our BN powder in comparison with talc which is a conventional typical extender and a conventional BN powder.

DETAILED DESCRIPTION

The following describes our powders, methods, and cosmetics in detail.

Our boron nitride powders are basically made up of flat-shaped primary particles, and are characterized by high hydrophilicity and high oil absorption.

The hydrophilicity is described first.

Various methods have been proposed for hydrophilicity evaluation. A typical method is to evaluate the hydrophilicity from the angle of contact between a powder and a liquid. With this evaluation method, however, quantitative evaluation is difficult, though qualitative evaluation of tendencies is possible.

In view of this, a water permeability test conforming to JIS A 6909 (Water Permeability Test B Method) that enables quantitative evaluation is employed, and the water permeation speed is specified to be not less than 1 $mm^2/s$ in the water permeability test. If the permeation speed is less than 1 $mm^2/s$, a sufficient amount of functional groups are not present on the surface of the BN powder, and satisfactory hydrophilicity cannot be obtained. The permeation speed is more preferably not less than 1.2 $mm^2/s$. The upper limit of the permeation speed is not particularly limited, and may be adequately set to about 5 $mm^2/s$.

A hydrophilic BN powder has a feature that there are many functional groups on its surface. A typical method of evaluating the functional groups on the surface is based on analysis on the amount of impurities. The impurities are mostly oxygen and carbon. Of these, oxygen is present on the surface of the BN powder as OH groups or carbonyl groups, and increases the hydrophilicity of the powder.

Moreover, since the leaching of B significantly damages the skin, it is desirable to reduce the amount of soluble B to less than or equal to 100 ppm. The amount of soluble B correlates with the specific surface area of the powder, and tends to increase when the specific surface area exceeds 10 $m^2/g$. It is therefore preferable to set the specific surface area to less than or equal to 10 $m^2/g$. Besides, if the specific surface area is larger, the surface activity increases, and the interparticle bond strength increases to create strongly aggregated particles. This causes a disadvantage of increased rough feeling. In this respect, too, it is preferable to set the specific surface area to less than or equal to 10 $m^2/g$. If the specific surface area is below 1 $m^2/g$, the particle diameter is excessively large, and a problem of degradation in feeling of use such as moist feeling or gloss arises. Hence, the specific surface area of the BN powder aggregate is preferably in a range from 1 $m^2/g$ to 10 $m^2/g$. The specific surface area of the BN powder aggregate is more preferably in a range from 2 $m^2/g$ to 5 $m^2/g$.

If the oxygen content in the BN powder exceeds 1.5 mass %, boron oxide as an impurity increases. This causes a disadvantage such as damage to the skin in the case where such BN is used in a cosmetic. Accordingly, the oxygen content is preferably less than or equal to 1.5 mass %, and more preferably less than or equal to 1.0 mass %.

Equally from a safety point of view, the pH of the BN powder is preferably neutral in a range from about 5 to 9. The pH of the BN powder is measured according to the Japanese Standards of Quasi-drug Ingredients 2006 (Yakuji Nippo Limited).

The oil absorption is described next.

The oil absorption is a factor closely related to the finish and sustainability of the cosmetic, and higher oil absorption is more preferable.

The oil absorption of talc or a conventional BN powder is only about 80 ml/100 g. In our powders, on the other hand, by using a polyoxyethylene surfactant in washing, the oil absorption of the BN powder can be increased to 100 ml/100 g or more. Here, since excessively high oil absorption causes a problem of large variations in viscosity, bulk density, and the like of the compound when manufacturing the cosmetic, the upper limit of the oil absorption is set to 500 ml/100 g. The oil absorption is preferably in a range from 150 ml/100 g to 400 ml/100 g.

FIG. 1 illustrates the oil absorbency of our BN powder (No. 1) in comparison with talc which is a conventional typical extender and a conventional BN powder. Our BN powder (No. 1) corresponds to No. 1 in Table 1 described later.

As illustrated in the drawing, our BN powder has significantly improved oil absorbency as compared with the conventional BN powder or talc.

As the polyoxyethylene surfactant, a hydrophilic surfactant including polyethylene ether, such as polyoxy ether type, ester type, or fatty acid ester, is advantageously applied.

The concentration of the polyoxyethylene surfactant in the washing liquid is preferably about 0.5 mass % to 2.5 mass % with respect to the BN powder to be washed.

The primary particles of BN are preferably flat-shaped with an average major diameter of 2 μm to 20 μm and a thickness of 0.05 μm to 0.5 μm.

Primary particles below 2 μm in average major diameter are difficult to be manufactured. Meanwhile, primary particles exceeding 20 μm exhibit orientation, which causes a decrease in density of the aggregate (an increase in porosity). If the thickness of the primary particles is below 0.05 μm, flat particles suitable for a cosmetic of 5 μm to 10 μm that can exhibit lubricity are not formed. If the thickness of the primary particles exceeds 0.5 μm, the transparency is lower and the plane surface cannot be maintained smoothly in the case where the cosmetic is applied to spread on the skin.

The proportion of the boron nitride powder in the cosmetic pigment is preferably 0.1 mass % to 70 mass %. If the proportion is below 0.1 mass %, the effect of improving the sustainability and the adhesion as desired is poor. If the proportion exceeds 70 mass %, the glittering appearance specific to the BN powder intensifies, and appropriate gloss cannot be attained.

Our manufacturing method is described next.

A high-purity BN powder having a turbostratic structure is prepared as a raw material. As used herein, the BN powder having a turbostratic structure means the BN powder that has an incompletely-crystallized structure which exhibits a X-ray diffraction pattern not with a sharp peak corresponding to a hexagonal system but with a broad peak.

Such a BN powder can be obtained by uniformly mixing boric acid and/or its dehydration product, urea and/or its compound (dicyandiamide, melamine, etc.), and boron carbide ($B_4C$) and heating the mixture in an inert gas atmosphere.

The obtained BN powder is then heat-treated at a temperature of 1500° C. to 2300° C. in an inert gas atmosphere and, after grinding, washed in a washing liquid containing a polyoxyethylene surfactant, to provide hydrophilic functional groups on the surface while removing B.

Here, since BN easily combines with oxygen, the treatment atmosphere is set to an inert gas atmosphere.

Moreover, the heating temperature of 1500° C. to 2300° C. is set for the following reason. If the treatment temperature is below 1500° C., a powder with sufficiently grown crystals cannot be obtained. If the treatment temperature exceeds 2300° C., defects are likely to occur and result in lower transparency.

A BN powder that is flat-shaped and slidable, has hydrophilicity and high oil absorption, and is ideal as an extender for liquid foundation can be obtained in this way.

Our BN powder is effective mainly for use as a cosmetic pigment for liquid foundation, but the following other uses are also possible.

The BN powder is suitable for use in makeup cosmetics such as base, face color, lipstick, eye shadow, eye liner, mascara, and manicure, and skin care cosmetics and body cosmetics such as cream, lotion, and pack.

The basic components of the above-mentioned cosmetics are not particularly limited, and may be conventionally well-known components so long as our BN powder is used instead of a BN powder or an inorganic powder (e.g. silicic anhydride, aluminum oxide, titanium oxide, zinc oxide, zirconium oxide) in the conventional components.

EXAMPLES

The following describes examples.

Example 1

100 parts by mass boric acid, 100 parts by mass melamine, and 10 parts by mass boron carbide were uniformly mixed in a mixing machine, and heated in an inert atmosphere to obtain a boron nitride powder having a turbostratic structure. The obtained boron nitride powder was heated to 2000° C. in a nitrogen atmosphere, and then cooled to a room temperature.

The obtained product was identified by an X-ray diffractometer and as a result determined to be highly crystalline BN.

After this, the BN powder was grinded to 100 μm or less using a pin mill device (made by Hosokawa Micron Corporation), and 1 kg of the BN powder was washed with a washing liquid that contains 1.0 mass % polyethylene ether as a surfactant with respect to the BN powder to be washed, and then dried. As a result, 632 g of the BN powder that has the amount of B less than or equal to 100 ppm and has functional groups on its surface was obtained.

Table 1 shows the quality evaluation results of the obtained BN powder.

Table 1 also shows the results of examining the hydrophilicity, the oil absorption, the amount of soluble B, and the pH of the obtained BN powder.

The results of the same examination on the conventional BN powder and talc are also shown in Table 1 for comparison.

The hydrophilicity, the oil absorption, and the amount of souble B of the BN powder were each measured as follows.

(1) Hydrophilicity

A water permeability test conforming to JIS A 6909 (Water Permeability Test B Method) was conducted to measure the water permeation speed.

In detail, using a powder wetting permeation analyzer PW-500 (made by Mitsuwa Frontech Corp.), 1 g powder was charged into a column of 10 mm in inside diameter, and the "wetting height" from the lower liquid contact surface was measured with time, to calculate the permeation speed.

(2) Oil Absorption

The oil absorption was measured by a test conforming to "Oil absorption" defined in JIS K 5101.

In detail, 2 g powder was metered on a watch glass, and refined linseed oil was added drop by drop from a burette. Upon each addition, the added linseed oil was kneaded using a spatula. This is repeated until the hardness reaches a smoothness level with no cracking or separation. The value obtained by converting the measurement to correspond to 100 g powder was set as the oil absorption.

(3) Amount of Soluble B

The amount of soluble B was measured in conformance with the Japanese Standards of Quasi-drug Ingredients 2006.

In detail, 2.5 g powder was metered in a Teflon® beaker, to which 10 ml ethanol was added and mixed well. After newly adding 40 ml boiled and cooled water and mixing them, the mixture was heated at 50° C. for 1 hour. The liquid was then filtered and B in the filtrate was measured.

(4) pH

The pH was measured in conformance with the Japanese Standards of Quasi-drug Ingredients 2006.

In detail, 10 ml ethanol was added to 2.5 g powder and mixed well. After newly adding 50 ml boiled and cooled water and mixing them, the mixture was filtered and the pH of the filtrate was measured.

[Table 1]

TABLE 1

|  | Extender | | |
|---|---|---|---|
|  | No. 1 | Conventional BN | Talc* |
| BN (%) | 99 | 99 | — |
| Average particle diameter (μm) | 5.8 | 5.4 | 5.2 |
| Oxygen content (mass %) | 1.2 | 0.8 | — |
| Specific surface area (m²/g) | 4.5 | 4.5 | 8.5 |
| Permeation speed (mm²/s) | 1.1 | 0.5 | 1.2 |
| Oil absorption (ml/100 g) | 152 | 86 | 72 |
| Amount of soluble B (ppm) | 56 | 78 | — |
| pH | 6.7 | 6.8 | 9.1 |

*Nippon Talc P-3

As shown in Table 1, our BN powder (No. 1) has high hydrophilicity and oil absorption and a low amount of soluble B, and is excellent in sustainability and spreadability.

Example 2

Various cosmetics of Examples 1 to 3 and Comparative Examples 1 to 4 shown below were produced using the BN powder No. 1 shown in Table 1.

Example 1

Water-In-Oil Emulsion Foundation

| (composition) | (mix proportion %) |
|---|---|
| boron nitride (No. 1 in Table 1) | 5.0 |
| diglyceryl isostearate | 1.0 |
| polyether-modified silicone | 1.0 |
| volatile silicone | 20.0 |
| vaseline | 3.0 |
| liquid paraffin | 6.0 |
| propyleneglycol dicaprylate | 4.0 |
| glycerine | 3.0 |
| maltitol | 3.0 |
| octyltriethoxysilane-treated titanium oxide (#1) | 8.0 |
| octyltriethoxysilane-treated red iron oxide | 0.2 |
| octyltriethoxysilane-treated yellow iron oxide | 0.8 |
| octyltriethoxysilane-treated black iron oxide | 0.1 |
| silicone gel (KSG-16 made by Shin-Etsu Chemical Co., Ltd.) | 2.0 |
| urethane powder (PLASTIC POWDER D-400 made by Toshiki Pigment Co., Ltd.) | 0.5 |
| sodium dehydroacetate | 0.05 |
| phenoxyethanol | 0.3 |
| purified water | remaining amount |

(#1) TIPAQUE CR-50 (made by Ishihara Sangyo Kaisha, Ltd.) coated with octyltriethoxysilane.

Example 2

Base

| (composition) | (mix proportion %) |
|---|---|
| boron nitride (No. 1 in Table 1) | 5.0 |
| polyether-modified silicone | 2.0 |
| dimethyl silicone (KF-96A (6CS) made by Shin-Etsu Chemical Co., Ltd.) | 5.0 |
| volatile silicone | 14.0 |
| octyl paramethoxycinnamate | 2.0 |
| dipropylene glycol | 2.0 |
| glycerine | 1.0 |
| sodium citrate | 0.5 |
| silicone-treated titanium oxide (#2) | 1.0 |
| silicone-treated fine particulate titanium oxide | 3.0 |
| silicone-treated red iron oxide | 0.4 |
| silicone-treated yellow iron oxide | 1.5 |
| silicone-treated black iron oxide | 0.2 |
| silicone-treated talc | 1.9 |
| ethanol | 10.0 |
| phenoxyethanol | 0.2 |
| purified water | remaining amount |

Example 3

Oil-In-Water Foundation

| (composition) | (mix proportion %) |
|---|---|
| boron nitride (No. 1 in Table 1) | 8.0 |
| 2% acrylic acid-alkyl methacrylate copolymer aqueous dispersion | 15.0 |
| 2% carboxyvinyl polymer aqueous dispersion | 15.0 |
| dipropylene glycol | 5.0 |
| edetate disodium | 0.05 |
| ethanol | 15.0 |
| polyoxyethylene(2) alkyl(12-16) ether phosphate | 0.5 |
| 2-ethylhexyl hydroxystearate | 5.0 |
| 2-amino-2-methyl-1-propanol | 0.5 |
| silicone-treated titanium oxide | 8.0 |
| red iron oxide | 0.2 |
| yellow iron oxide | 1.0 |
| black iron oxide | 0.1 |
| cross-linked type silicone powder (Trefil E-506C made by Dow Corning Toray Co., Ltd.) | 1.5 |
| 2% xanthan gum dispersion | 15.0 |
| phenoxyethanol | 0.2 |
| sodium dehydroacetate | 0.05 |
| purified water | remaining amount |

Comparative Examples 1 to 3

Respective cosmetics having the compositions of the above-mentioned Examples 1 to 3 except the BN powder.

Comparative Example 4

A cosmetic in which the conventional BN powder shown in Table 1 is used instead of the BN powder of Example 1.

Table 2 shows the results of examining the sustainability and the spreadability of each of these cosmetics.

To evaluate the above-mentioned various properties, a research panel of 20 cosmetic evaluation specialists used our products and the comparative products and made evaluation on the following 5-point scale. The average score of the whole research panel was then calculated, and each product was rated according to the following four levels.

Evaluation Scale
5: very good
4: good
3: fair
2: poor
1: very poor

Rating scale
level A: greater than or equal to 4.5
level B: greater than or equal to 3.5, and less than 4.5
level C: greater than or equal to 2.5, and less than 3.5
level D: less than 2.5

TABLE 2

|  | Sustainability | Spreadability |
| --- | --- | --- |
| Example 1 | A | A |
| Example 2 | A | A |
| Example 3 | A | A |
| Comparative Example 1 | B | C |
| Comparative Example 2 | B | C |
| Comparative Example 3 | B | C |
| Comparative Example 4 | C | C |

As shown in Table 2, the products using our BN powder as a cosmetic extender are rated higher than the conventional products, in both sustainability and spreadability.

The invention claimed is:

1. A hydrophilic and highly oil absorbent boron nitride powder, washed in a liquid that contains surfactant, comprising flat-shaped primary particles of BN and an aggregate of the primary particles,
wherein a water permeation speed is not less than 1 mm$^2$/s, and oil absorption is 100 ml/100 g to 500 ml/100 g.

2. The hydrophilic and highly oil absorbent boron nitride powder according to claim 1,
wherein the primary particles of BN are flat-shaped with an average major diameter of 2 μm to 20 μm and a thickness of 0.05 μm to 0.5 μm.

3. The hydrophilic and highly oil absorbent boron nitride powder according to claim 1,
wherein an amount of soluble boron is less than or equal to 100 ppm.

4. The hydrophilic and highly oil absorbent boron nitride powder according to claim 2,
wherein a specific surface area is 1 m$^2$/g to 10 m$^2$/g, and an oxygen content is less than or equal to 1.5 mass %.

5. A method for manufacturing a hydrophilic and highly oil absorbent boron nitride powder, the method comprising:
heating at least one of boric acid and a dehydration product thereof, at least one of urea and a compound thereof, and boron carbide in an inert atmosphere to obtain a boron nitride powder having a turbostratic structure;
heat-treating the obtained boron nitride powder at a temperature of 1500° C. to 2300° C. in an inert atmosphere;
grinding the heat-treated boron nitride powder; and
washing primary particles of boron nitride obtained as a result of the grinding in a washing liquid that contains a surfactant, and drying the washed primary particles.

6. A cosmetic comprising the boron nitride powder according to claim 1.

7. The cosmetic according to claim 6,
wherein an amount of the boron nitride powder contained in the cosmetic is 0.1 mass % to 70 mass %.

8. The cosmetic according to claim 6,
wherein the cosmetic is liquid foundation.

* * * * *